United States Patent
Randolph

(10) Patent No.: US 10,206,758 B2
(45) Date of Patent: Feb. 19, 2019

(54) PROPHY ANGLE WITH TRANSLATING PADDLE SYSTEM AND METHOD FOR METERED DISPENSING OF A PROPHYLAXIS MEDIUM WITH TACTILE AND AURAL FEEDBACK

(76) Inventor: Bradley A. Randolph, Fort Madison, IA (US)

( * ) Notice: Subject to any disclaimer, the term of this patent is extended or adjusted under 35 U.S.C. 154(b) by 0 days.

(21) Appl. No.: 12/337,899

(22) Filed: Dec. 18, 2008

(65) Prior Publication Data

US 2009/0098505 A1 Apr. 16, 2009

Related U.S. Application Data

(60) Provisional application No. 61/038,944, filed on Mar. 24, 2008.

(51) Int. Cl.

| A61C 1/12 | (2006.01) |
|---|---|
| A46B 9/00 | (2006.01) |
| A61C 17/00 | (2006.01) |
| A61C 17/22 | (2006.01) |

(52) U.S. Cl.
CPC ............... *A61C 1/12* (2013.01); *A46B 9/005* (2013.01); *A61C 17/005* (2013.01); *A46B 2200/01* (2013.01); *A61C 17/227* (2013.01)

(58) Field of Classification Search
CPC .. A61C 1/12; A61C 1/087; A61C 3/06; A61C 17/005; A61C 17/227
USPC ............................................... 433/80, 82, 87
See application file for complete search history.

(56) References Cited

U.S. PATENT DOCUMENTS

| 2,300,828 | A | 11/1942 | Goldenberg | |
|---|---|---|---|---|
| 5,642,994 | A * | 7/1997 | Chipian et al. | 433/82 |
| 5,871,353 | A | 2/1999 | Pierce | |
| 5,911,577 | A | 6/1999 | Henrikson | |
| 6,257,886 | B1 | 7/2001 | Warner | |
| 6,632,090 | B1 | 10/2003 | Randolph | |
| 6,902,397 | B2 | 6/2005 | Farrell et al. | |
| 7,070,412 | B2 | 7/2006 | Stadeker | |
| 7,338,285 | B1 | 3/2008 | Balaban | |
| 7,510,396 | B2 | 3/2009 | Lee et al. | |
| 2006/0246395 | A1 | 11/2006 | Pond | |
| 2007/0111159 | A1* | 5/2007 | Stadeker | 433/82 |
| 2008/0261171 | A1 | 10/2008 | Michaelian | |
| 2008/0311541 | A1 | 12/2008 | Carron et al. | |

* cited by examiner

*Primary Examiner* — Ralph Lewis
(74) *Attorney, Agent, or Firm* — Simmons Perrine Moyer Bergman PLC

(57) ABSTRACT

A disposable prophy angle with an accessible and replaceable internal collapsible prophylaxis bladder and a push button and plunger/paddle combination to force a metered amount of prophylaxis medium into the prophy angle while providing audible and/or tactile feedback.

10 Claims, 6 Drawing Sheets

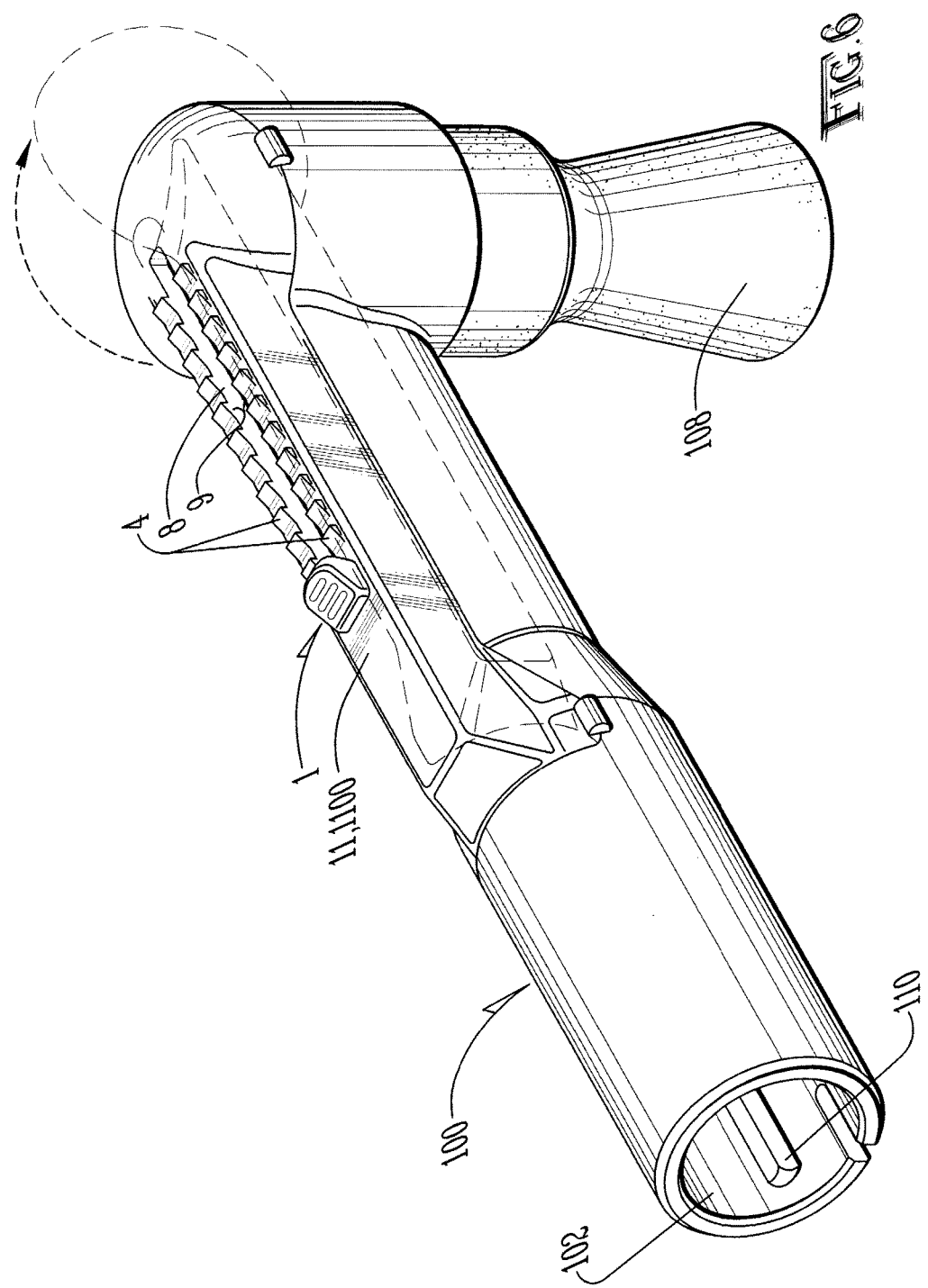

PROPHY ANGLE WITH TRANSLATING PADDLE SYSTEM AND METHOD FOR METERED DISPENSING OF A PROPHYLAXIS MEDIUM WITH TACTILE AND AURAL FEEDBACK

CROSS REFERENCE TO RELATED APPLICATIONS

This application claims the benefit of the filing date of provisional patent application entitled "PROPHY ANGLE WITH LEVER AND PADDLE DELIVERY MECHANISM FOR DENTIFRICE", having Ser. No. 61/038,944, which was filed on Mar. 24, 2008, by Bradley A. Randolph, which provisional patent application is incorporated herein in its entirety by this reference.

FIELD OF THE INVENTION

The present invention generally relates to prophy angles used in dentistry.

BACKGROUND OF THE INVENTION

Devices that help aid in the professional cleaning or polishing of teeth have been around the industry for years. These devices have been generally known as prophy angles. Prophy angles have been through various stages of development and improvement from re-usable to disposable. Currently within the industry, the disposable angle has enjoyed much success due to its low cost, simplification and most importantly, single use which virtually eliminates cross contamination risk to patient and provider. The downfall of current delivery systems requires the use of a separate dentifrice to complete the task, thus creating a loss of efficiency, increase in overall costs and packaging, and ultimately an increase in risk to patient and provider to contamination. More recent developments in prophy angle design have attempted to incorporate the prophylaxis medium within the prophy angle. These presentations have utilized varying designs from auger/baffle to piston U.S. Pat. No. 5,871,353 to plunger U.S. Pat. No. 6,257,886 to systems that utilize a threaded shaft and spring loading U.S. Pat. No. 6,902,397, and U.S. Pat. No. 6,632,090. All of these systems force the dentifrice to occupy the bulk of the prophy angle housing. All designs have shown to be somewhat complex, creating cost and difficulty becoming implemented within the market place. One more recent design attempts to offset the drive shaft to allow for less complexity in delivery U.S. Pat. No. 7,070,412. However, persistent deficiencies in prior art designs have failed to teach a system that will simultaneously allow for incorporation of a prophylaxis medium into the prophy angle, allow for its controlled dispensing with both tactile and aural feedback regarding amount and rate of dispensing, and be simplistic enough in design to adapt to the market place.

Consequently, there exists a need for improved methods and systems for cost effectively delivering a prophylaxis medium through a prophy angle.

SUMMARY OF THE INVENTION

It is an object of the present invention to provide a system and method for dispensing prophylaxis medium in an efficient manner.

It is a feature of the present invention to utilize an internally integrated collapsible bladder pre-filled with prophylaxis medium, together with a translatable push button and a connected plunger or paddle.

It is another feature of the present invention to include a series of ridges for engaging with the push button and metering delivery of prophylaxis medium while simultaneously preventing "back-peddling" of the push button.

It is yet another feature of the present invention to provide a combination of a push button and ridges being so configured that a tactile feel and/or audible "click" or other indication occurs each time the plunger/paddle is advanced to a new forward location.

It is another feature of the present invention to include a revenue-sharing model whereby a provider of consumer products and/or services shares revenue with an educational or civic institution which carries out the simulation experience.

It is an advantage of the present invention to provide a relatively inexpensive easy-to-use prophy angle with an integrated prophylaxis delivery mechanism.

The present invention is designed to satisfy the aforementioned needs, provide the previously stated objects, include the above-listed features, and achieve the already articulated advantages.

Accordingly, the present invention is a system and method including providing a plunger-actuated collapsible prophylaxis bladder inside a prophy angle housing which provides for relatively inexpensive easy delivery of prophylaxis medium.

BRIEF DESCRIPTION OF THE DRAWINGS

The invention may be more fully understood by reading the following description of the preferred embodiments of the invention, in conjunction with the appended drawings wherein:

FIG. 6 is a perspective view of another embodiment of the prophy angle of the present invention where the dashed lines are phantom lines showing the top of the prophy angle in a pivoted up or open position where the direction of pivoting is shown by the dashed arrow.

DETAILED DESCRIPTION OF THE INVENTION

Figure 1:
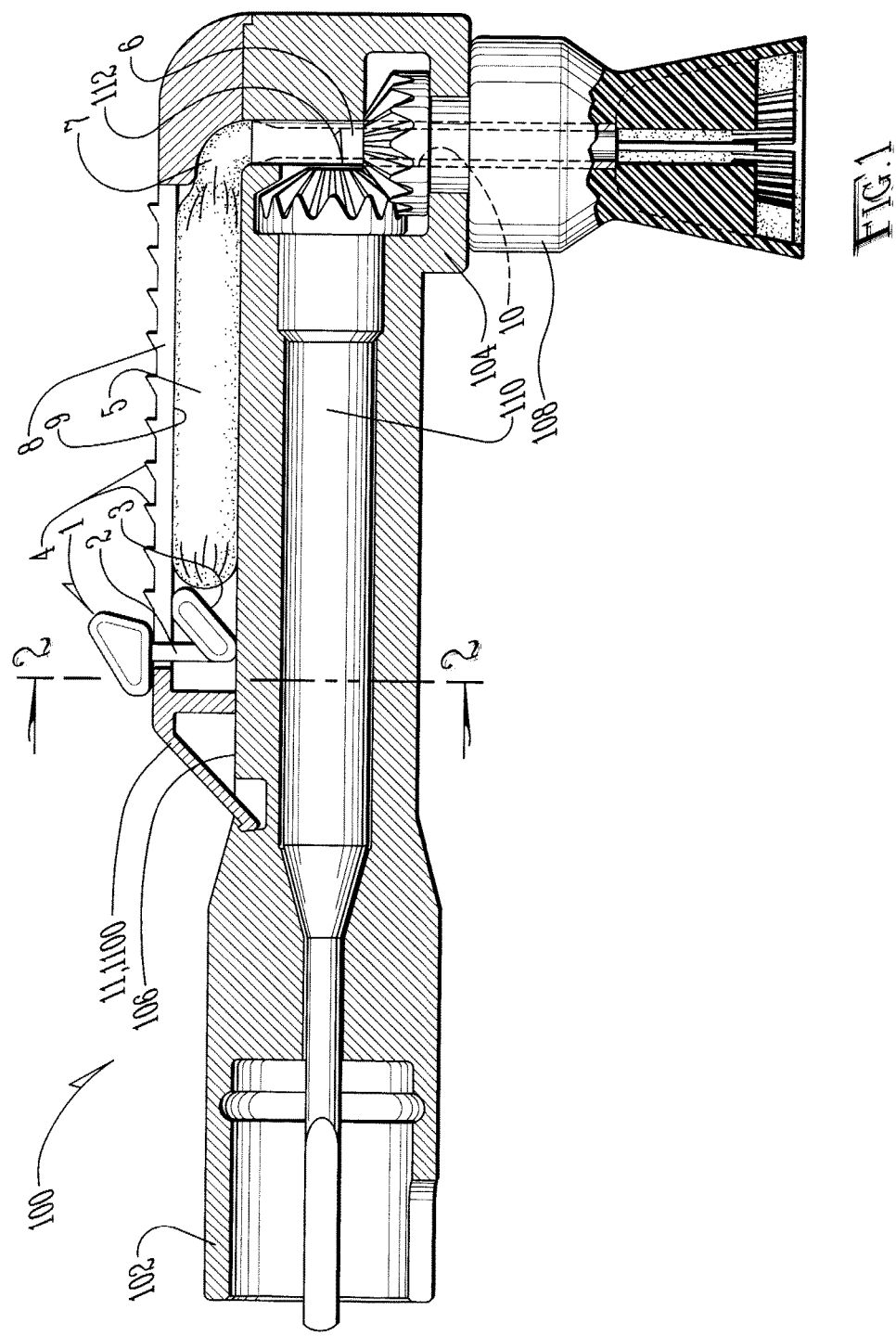
FIG. 1 is a side cutaway view of a prophy angle of the present invention where the vertical dashed line labeled 2-2 is a line along which the cross-sectional view of FIG. 2 was taken.

Now referring to the drawings, wherein like numerals refer to like matter throughout, and more specifically to FIG. 1, there is shown a prophy angle generally designated 100 which can be generally constructed of the same materials and in the same general manner as prior art prophy angles. It should now be noted that in one embodiment, the prophy angle 100 of the present invention need not be a professional device, and the present invention is intended to include rotary and reciprocating toothbrushes as well. Prophy angle 100 may have a drive connection end 102 which would connect to a standardized pneumatic prophy angle drive system (not shown), or other means for driving a plurality of detachable and disposable prophy angles, which system is well known in the art, which could include electrical prophy angle drive systems or self-contained battery-powered handheld prophy angle drive systems or other means for driving a plurality of detachable and disposable prophy angles. Drive connection end 102 could be omitted if the prophy angle 100 were incorporated into a larger device such as a personal electric toothbrush. Opposing drive connection end 102 is cup end 104. Top side 106 of prophy angle 100 is shown with innovative features thereon, such as: push button 1, which could be a plastic material the same as or similar to the prophy angle 100 housing or other suitable material and configuration so as to provide for a tactile interaction between a user's finger or thumb and a paddle or plunger 3 via a connector 2 which transmits force applied by the finger at the push button 1 to the paddle 3 and then into the prophylaxis medium in the collapsible bladder 5. Collapsible bladder 5 is disposed under and adjacent to raised ridges 4, which also interact with the push button 1. Collapsible bladder 5 is coupled to a connecting tube 6, which provides a pathway for prophylaxis medium to flow to the prophy cup 108 or toothbrush. Connecting tube 6 couples to a pathway through the gear head pathway 10 which extends through a central void in the gear head 112. Collapsible bladder 5 is disposed in a reservoir 7 which is disposed in a raised portion of a housing on or integrated with the housing of the prophy angle 100. A removable housing cap 11 is shown for providing access to the collapsible bladder 5 in the reservoir 7. Removable housing cap 11 or lid is detachable, but other arrangements, such as a hinged or sliding, or other suitable ways to permit access into the reservoir 7 could also be used. Removable housing cap 11 could be similar to other snap-out or hinged access doors existing in prior art prophy angles.

Collapsible bladder 5 could be a flexible bag-like bladder or instead, it could be substituted with a syringe, a plunger or other variable volume structure which can eject matter from therein when a force is applied. Items 8 and 9 are discussed below with respect to FIG. 3.

Figure 2:
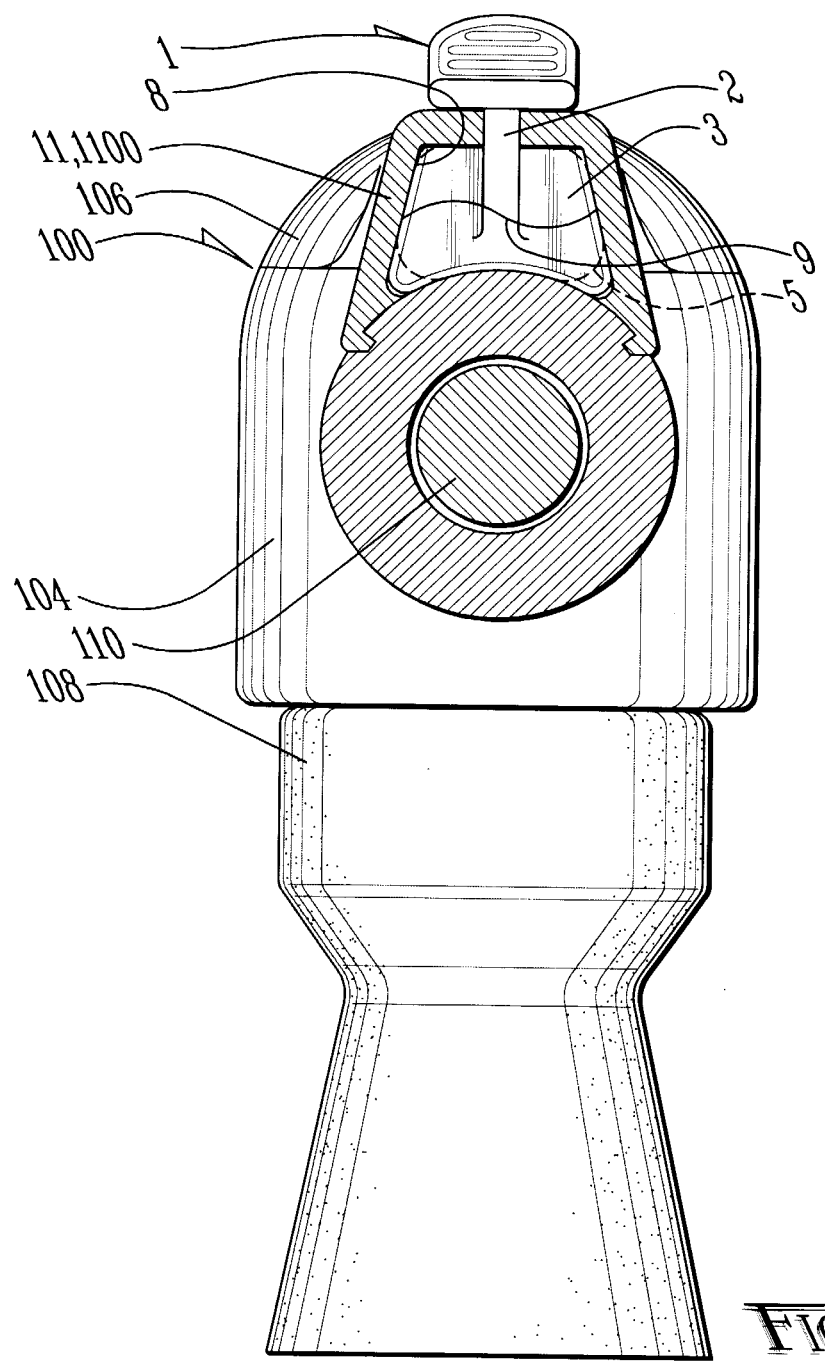
FIG. 2 is a cross-sectional view of the prophy angle of the present invention taken on line 2-2 of FIG. 1.

Now referring to FIG. 2, there is shown a cross-sectional view of the prophy angle 100 taken on line 2-2 of FIG. 1, which shows the drive member 110 which couples at drive connection end 102 to a prophy angle drive system, which is a commercially available product.

Figure 3:
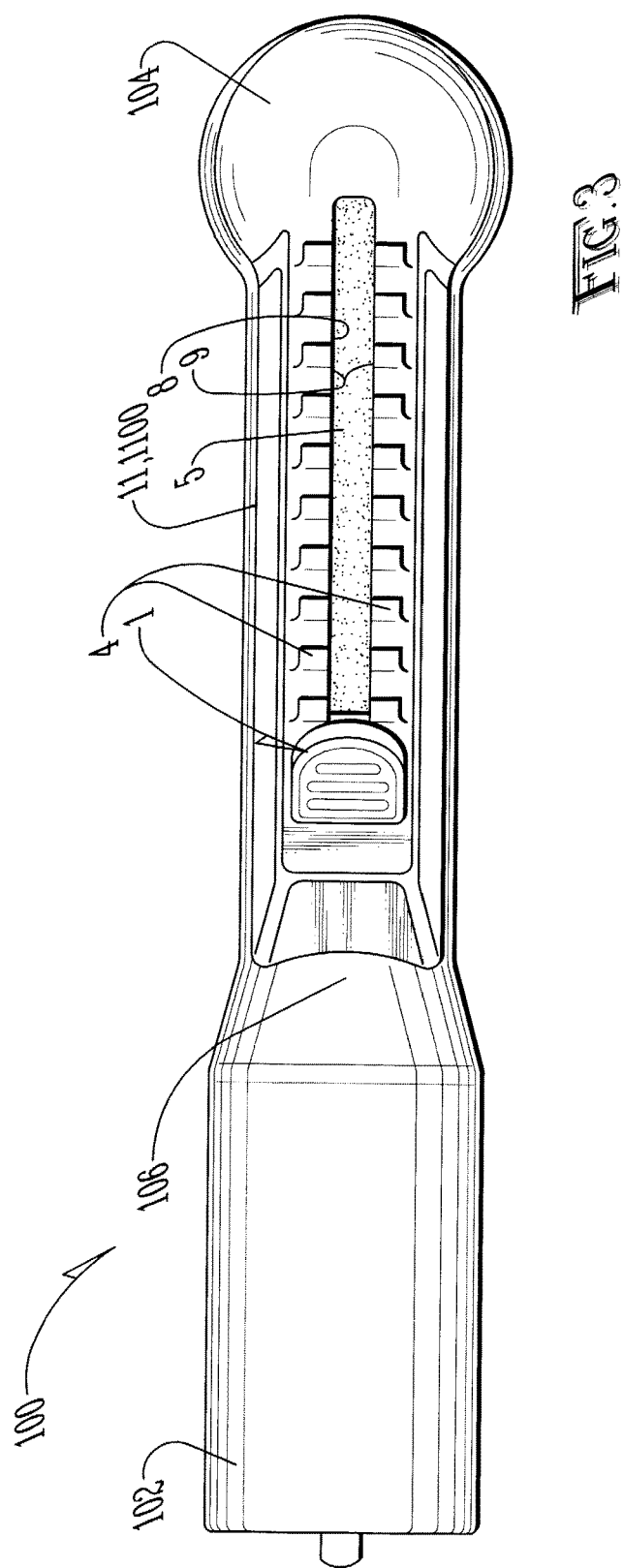
FIG. 3 is a top view of the prophy angle of the present invention.

Now referring to FIG. 3, there is shown a top view of the prophy angle 100 of FIG. 1, which shows cut-out channel 8 in the removable housing cap 11 to reveal the collapsible bladder top side 9. Raised ridges 4 are shown on either side of the cut-out channel 8. Raised ridges 4 cooperate with the push button 1 to visually, tactilely, and audibly notify a user of the prophy angle 100 of an amount of prophylaxis medium which has been forced out of the collapsible bladder 5.

Figure 4:
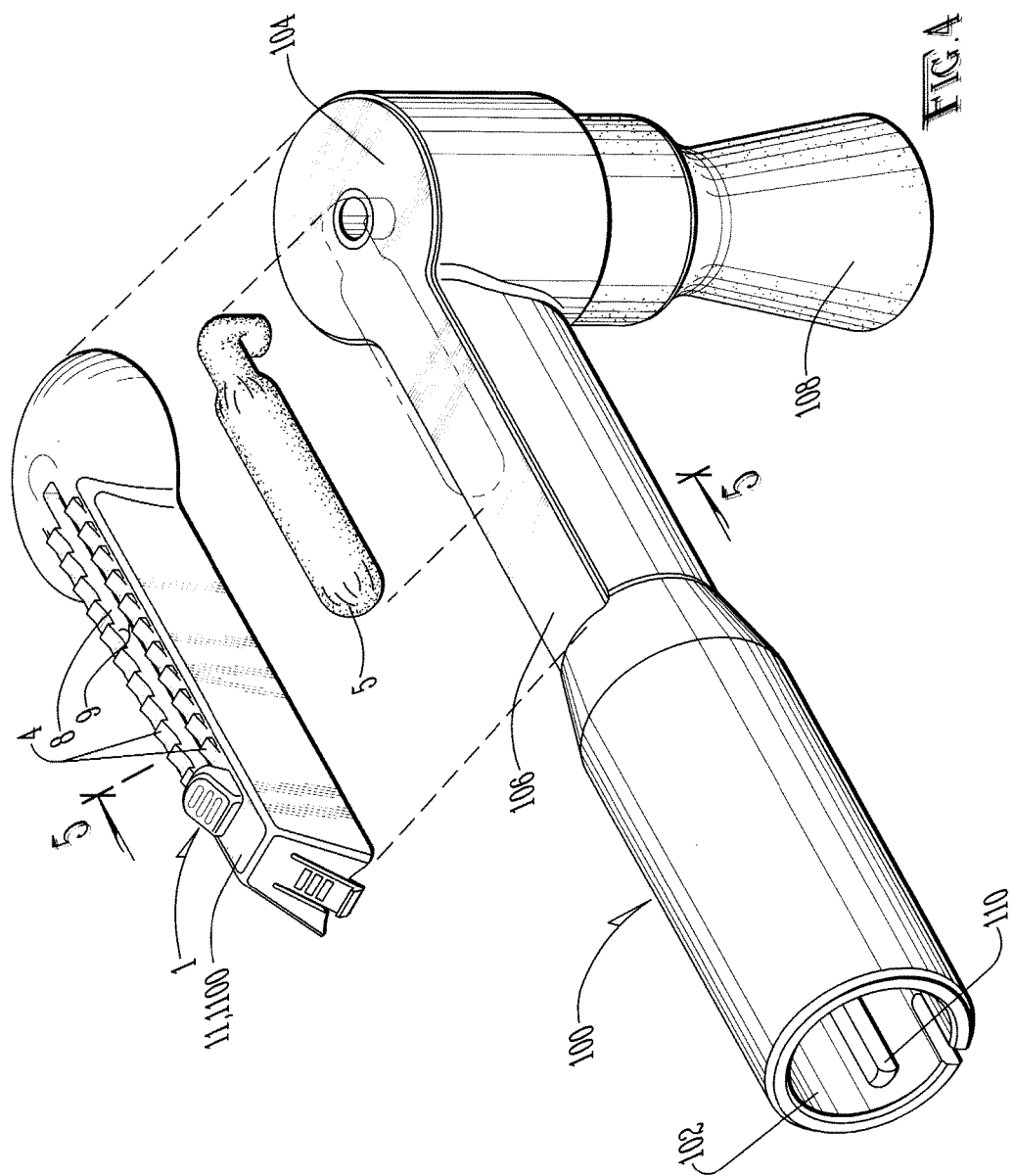
FIG. 4 is an exploded perspective view of an embodiment of the present invention which has an internal to the prophy angle disposable prophylaxis reservoir therein.

Now referring to FIG. 4, there is shown an embodiment of the present invention where a disposable and removable pouch 5 is located under a removable housing cap 11 or lid 1100, such that the disposable and removable pouch 5 can be removed when emptied and replaced with a full disposable removable pouch 5 for further delivery of prophylaxis media. Note that the lid 1100 could be just above the shaft 110 containing portion 102 of the prophy angle; however, it could extend to include the entire top of the cup end 104, thereby exposing top of the cup end 104 housing the gear head 112. Note FIG. 4 shows a top portion of the cup end 104; however, it should be understood that this is optional and in some embodiments of the present invention, removal of the removable housing cap 11 would result in exposing the gear head 112.

Figure 5:
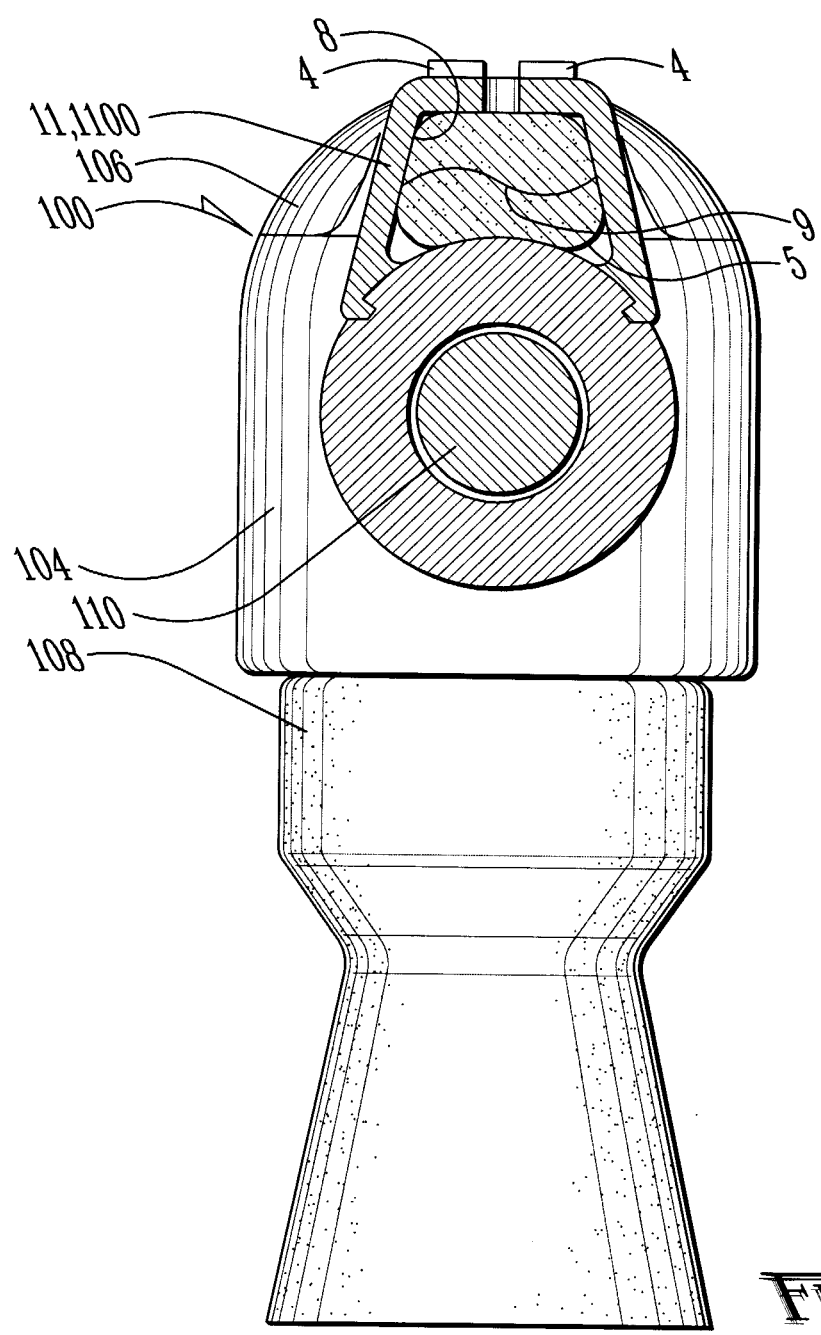
FIG. 5 is a cross-sectional view of the prophy angle of FIG. 4 take on line 5-5 of FIG. 4.

Now referring to FIG. 5, there is shown a cross-sectional view of the prophy angle of FIG. 4 taken on line 5-5 after the removable housing cap 11 has been replaced or closed. The button 1 and paddle 3 are not shown so that the disposable removable collapsible bladder 5 can be seen to be within the main body of the prophy angle.

Now referring to FIG. 6, there is shown an alternate embodiment of the present invention where the lid 1100 is not a snap-off lid, but a hinged lid. The dashed arrows show the direction of rotation of the lid 1100 when opened, and the dashed lines are phantom lines showing the location and orientation of the lid 1100 when in the open position. Items 11 and 1100 are shown in the figures as referring to the same structure. It should be noted that the structure of these is nearly identical, and the term "removable housing cap 11" is used primarily to suggest a removable cap, and the term "lid 1100" is intended to convey the notion of a pivoting door or lid. It is believed that a person skilled in the art will understand these variations.

It should be noted that the removable housing cap 11 and lid 1100 are shown as elevated above a normal top surface of a prophy angle. This is just one embodiment of the present invention. It should be understood that all of the structure disclosed above the top side 106 in FIG. 1 could be included in the prophy angle itself, and access to the bladder 5 could be made through a hinged section of the top of the prophy angle; i.e., it should be understood that embedding the system of the present invention into a typical prophy angle housing is included within the scope of the present invention. It is believed that a raised or exterior removable housing cap 11 may be preferred for manufacturing ease.

In operation, the dental professional removes the removable housing cap 11 or opens up the lid 1100, (or opens the hinged section of the prophy angle top side where the present invention is embedded within the prophy angle) exposes the reservoir 7, inserts a collapsible bladder 5, and then replaces the removable housing cap 11 or closes the hinged lid 1100 (section of the prophy angle top), and then attaches the prophy angle 100 to a prophy angle drive system and begins a procedure on a patient. It should be noted that the collapsible bladder 5 could be incorporated by the manufacturer into the prophy angle 100, thereby eliminating the need for having the dental professional insert the collapsible bladder 5. Prophylaxis medium is dispensed by occasionally incrementally moving the push button 1 forward (toward the cup end 104) through the cut-out channel 8. As the push button 1, coupled with the paddle 3 via connector 2, is pushed forward, the paddle 3 forces out of the collapsible bladder 5, prophylaxis medium via connecting tube 6 and passes through the gear head pathway 10 and into the prophy cup 108, toothbrush or other tooth-engaging means where it is available for its intended use.

Definitions

The term "prophylaxis medium" is used throughout this description and is intended to be construed in the claims as including dentifrice, toothpaste or other abrasive or lubricating matter applied to a tooth.

The term "prophy angle" is used throughout this description and is intended to be construed in the claims as professional disposable device for polishing teeth.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

I claim:

1. An apparatus for providing dentifrice into a tooth-cleaning means comprising:
   a longitudinal section having a longitudinal axis with a drive member disposed therein which is substantially parallel with the longitudinal axis;
   a head adjacent to said longitudinal section, said head having a tooth-engaging means which is oriented substantially perpendicular to the longitudinal axis and is configured to engage a tooth and remove matter from the tooth when the drive member is driven and the tooth-engaging means is in contact with the tooth;
   said longitudinal section having an exterior longitudinal section surface and sized and configured to be held and manipulated by a human hand and further comprising:
   a removable lid configured to be disposed on said exterior longitudinal section surface:
   a variable volume structure is disposed inside a fixed volume cavity defined by said exterior longitudinal section surface and said removable lid;
   said removable lid having a slot therein extending above the variable volume structure which is sized and configured to permit visual inspection of the variable volume structure during operation;
   a passageway configured to transport prophylaxis medium from the variable volume structure to the tooth-engaging means;
   finger-engaging member configured for transferring a longitudinal prophylaxis media expelling force from a finger to the variable volume structure;
   a plurality of exterior lid surface deviations in said removable lid;
   said finger-engaging member configured to be manually pushed longitudinally toward the head while causing the variable volume structure to decrease in volume and thereby expel prophylaxis medium into said tooth-engaging means in a metered manner, depending upon an extent of a distance of travel of the finger-engaging member;
   wherein the variable volume structure is a means for converting a longitudinal force into an increase in pressure to force prophylaxis medium into the tooth-engaging means;
   wherein the means for converting a longitudinal force is a collapsible bladder;
   wherein the tooth-engaging means is a prophy cup;
   wherein the plurality of exterior lid surface deviations and the finger-engaging member further cooperate to simultaneously provide to a user of the apparatus:
   tactile notification of passage of the finger engaging member beyond one of said plurality of exterior lid surface deviations; and
   aural notification of passage of the finger engaging member beyond one of said plurality of exterior lid surface deviations.

2. The apparatus of claim 1 wherein the passageway configured to transport prophylaxis medium has a neck section which is substantially parallel to the longitudinal axis and a head section which is substantially perpendicular to the longitudinal axis, and where the head section coaxially extends through a central portion of a gear head disposed in the head and configured to transfer motion of the drive member into motion of the tooth-engaging means.

3. The apparatus of claim 2 wherein the finger-engaging member slides through a slot in the top side of the removable lid, where the slot is disposed above the collapsible bladder and permits visual inspection of the prophylaxis material when the collapsible bladder is made of a transparent material.

4. The apparatus of claim 3 wherein the finger-engaging member makes a clicking sound when being advanced forward past one of the plurality of exterior lid surface deviations.

5. An apparatus for providing dentifrice into a tooth-cleaning means comprising:
   means for housing a drive shaft with a longitudinal axis and gears to cause a tooth-polishing means to turn about an axis which is substantially perpendicular to the longitudinal axis;
   said means for housing configured to be held and manipulated by a human hand and comprising an exterior surface;
   a removable lid configured to be disposed on said exterior surface;
   a variable volume structure is disposed inside a fixed volume cavity defined by said exterior surface and said removable lid;
   said removable lid having a slot therein extending above the variable volume structure which is sized and configured to permit visual inspection of the variable volume structure during operation;
   a passageway configured to transport dentifrice from the variable volume structure to the tooth polishing means; and
   means for simultaneously:
   1. causing a decrease in volume and thereby expelling dentifrice into said tooth polishing means;
   2. producing an aural notification of passage of the finger engaging member beyond one of said plurality of protuberances;
   3. producing a tactile notification of passage of the finger engaging member beyond one of said plurality of protuberances; and
   4. providing a graduated visual notification of expelling dentifrice.

6. An apparatus for providing dentifrice into a tooth-cleaning means comprising:
   a longitudinal section having a longitudinal axis with a drive member disposed therein which is substantially parallel with the longitudinal axis;
   a head adjacent to said longitudinal section, said head having a prophy cup which is oriented substantially perpendicular to the longitudinal axis and is configured to engage a tooth and remove matter from the tooth when the drive member is driven and the prophy cup is in contact with the tooth;
   said longitudinal section having an exterior surface and sized and configured to be held and manipulated by a human hand and further comprising:
   a removable lid configured to be disposed on said exterior surface;
   a variable volume structure is disposed inside a fixed volume cavity defined by said exterior surface and said removable lid;
   said removable lid having a slot therein extending above the variable volume structure which is sized and configured to permit visual inspection of the variable volume structure during operation;

a passageway configured to transport prophylaxis medium from the variable volume structure to the prophy cup;

finger-engaging member configured for transferring a longitudinal prophylaxis media expelling force from a finger to the variable volume structure;

a plurality of exterior surface deviations in said removable lid;

said finger-engaging member configured to be manually pushed longitudinally toward the head while causing the variable volume structure to decrease in volume and thereby expel prophylaxis medium into said prophy cup in a metered manner, depending upon an extent of a distance of travel of the finger-engaging member;

wherein the variable volume structure is sized, located and configured for converting a longitudinal force into an increase in pressure to force prophylaxis medium into the prophy cup;

wherein the variable volume structure comprises a collapsible bladder;

wherein the plurality of exterior surface deviations are a plurality of protuberances on a top side of the removable lid;

wherein the plurality of protuberances are configured to contact the finger-engaging member and to limit backward travel of the finger-engaging member;

wherein the plurality of protuberances and the finger-engaging member further cooperate to simultaneously provide to a user of the apparatus:

tactile notification of passage of the finger engaging member beyond one of said plurality of protuberances; and aural notification of passage of the finger engaging member beyond one of said plurality of protuberances.

7. The apparatus of claim 6 further wherein said removable lid has a latch member thereon which is configured to mate with a void in said exterior surface.

8. The apparatus of claim 6 wherein the passageway configured to transport prophylaxis medium has a neck section which is substantially parallel to the longitudinal axis and a head section which is substantially perpendicular to the longitudinal axis, and where the head section coaxially extends through a central portion of a gear head disposed in the head and configured to transfer motion of the drive member into motion of the prophy cup.

9. The apparatus of claim 8 wherein the finger-engaging member slides through a slot in the top side of the exterior surface, where the slot is disposed above the collapsible bladder and permits visual inspection of the prophylaxis material when the collapsible bladder is made of a transparent material.

10. The apparatus of claim 9 wherein the finger-engaging member makes a clicking sound when being advanced forward past one of the plurality of protuberances.

* * * * *